United States Patent [19]

Moore et al.

[11] Patent Number: 4,505,888

[45] Date of Patent: Mar. 19, 1985

[54] TRACER FOR CIRCULATION DETERMINATIONS

[75] Inventors: Herbert Moore, Wayland, Mass.; Stephen Santos, Manchester, N.H.; Robert D. Wysong, Wilmington, Del.

[73] Assignee: E. I. Du Pont de Nemours & Company, Wilmington, Del.

[21] Appl. No.: 498,867

[22] Filed: May 27, 1983

[51] Int. Cl.³ .................... A61K 43/00; A61K 49/00
[52] U.S. Cl. ................................. 424/1.1; 424/9; 521/25; 523/201
[58] Field of Search ............. 424/1.1, 9; 521/25; 523/201

[56] References Cited

U.S. PATENT DOCUMENTS

| | | | |
|---|---|---|---|
| 2,748,057 | 5/1956 | Goren | 196/221 |
| 2,749,251 | 6/1956 | Shapiro | 117/33.5 |
| 2,809,938 | 10/1957 | Goren et al. | 252/422 |
| 2,968,721 | 1/1961 | Shapiro et al. | 250/43.5 |
| 3,061,510 | 10/1962 | Numerof et al. | 167/51 |
| 3,121,041 | 2/1964 | Stern et al. | 167/51 |
| 3,147,225 | 9/1964 | Ryan | 252/301.1 |
| 3,154,500 | 10/1964 | Jansen, Jr. et al. | 252/301.1 |
| 3,155,622 | 11/1964 | Kazenas et al. | 252/62.5 |
| 3,156,532 | 11/1964 | Doering et al. | 23/252 |
| 3,159,545 | 12/1964 | Kidwell et al. | 167/83 |
| 3,161,601 | 12/1964 | Barton | 252/301.1 |
| 3,238,139 | 3/1966 | Fischer et al. | 252/301.1 |
| 3,249,551 | 5/1966 | Bixby | 252/301.1 |
| 3,329,817 | 7/1967 | Walz | 250/106 |
| 3,334,050 | 8/1967 | Grotenhuis et al. | 252/301.1 |
| 3,342,910 | 9/1967 | Ishihara et al. | 264/5 |
| 3,364,148 | 1/1968 | Kivel et al. | 252/301.1 |
| 3,366,573 | 10/1965 | Feuer | 252/301.1 |
| 3,399,979 | 9/1968 | Hamling | 23/347 |
| 3,403,008 | 9/1968 | Hamling | 23/344 |
| 3,428,568 | 2/1969 | Harker et al. | 252/301.1 |
| 3,492,146 | 1/1970 | Young et al. | 117/62.2 |
| 3,716,490 | 3/1973 | Van de Voorde | 252/301.1 |
| 3,746,650 | 7/1973 | Lahr et al. | 252/301.1 |
| 3,778,295 | 12/1973 | Smith et al. | 117/100 B |
| 4,107,283 | 8/1978 | Pratt et al. | 424/1 |

FOREIGN PATENT DOCUMENTS

| 2530449 | 1/1984 | France | 424/1.1 |
|---|---|---|---|
| 917649 | 2/1963 | United Kingdom | |

Primary Examiner—Christine M. Nucker
Attorney, Agent, or Firm—Sewall P. Bronstein; George W. Neuner

[57] ABSTRACT

An improved tracer particle is described comprising an ion exchange core having a polymer coating thereon, the coated ion exchange core having a reaction site capable of reacting with a compound containing an oxirane group, said coated ion exchange core having been treated with a compound containing an oxirane group to react with said coated ion exchange core causing an increase in mass of the tracer particle. Preferably, the ion exchange core is labelled with a radionuclide. These particles have improved characteristics including improved stability against leaching and improved handling properties. Such particles are useful in circulatory determinations involving the injection of the particles as a suspension in a physiologically acceptable carrier or medium into the circulatory system of animals.

46 Claims, No Drawings

TRACER FOR CIRCULATION DETERMINATIONS

FIELD OF THE INVENTION

This invention relates to particulate tracer materials having utility in circulatory determinations in animals or in the chemical process industries to detect or measure fluid flow, and particularly to such tracer materials comprising a polymer coated ion exchange core that has been labelled with a radioactive nuclide and treated with a compound containing an oxirane group.

BACKGROUND OF THE INVENTION

Various methods for producing particles carrying radioactive nuclides are known. One method, disclosed in U.S. Pat. No. 3,334,050, comprises the application of high temperatures for sealing nuclides into the interstices of ion exchange cores by carbonizing the core. Using this method it has been found difficult to obtain a high yield of uniform and desired size cores because of the difficulty in controlling shrinkage of the particles. In addition, certain nuclides such as Mercury$^{203}$ or Iodine$^{125}$ are extremely volatile at temperatures used for carbonization and thus losses of these nuclides would be expected to occur. Furthermore, it has been found in practice that particles produced in this manner when utilized as an injectable preparation in animal research tend to agglomerate both in an injectable preparation and in vivo thus comprising test results.

Another technique that is described in U.S. Pat. No. 3,492,147 uses a non-reactive or inert substrate (e.g., sand, glass, etc.) to which a monomeric coating containing radioactive nuclides is applied and is polymerized by extraction of a catalyst from an acid bath which is contacted with monomer coated particles. It has been found in practice that with this process substantial undesired bulk polymerization occurs, which limits the usefulness of the product.

A further process of the prior art involves the incorporation of $^{51}$Cr acetylacetonate (a chelating agent) into polystyrene and polystyrene vinyl lattices in toluene (non ion exchange resin) by a process called emulsion polymerization. This process tends to produce particles of very small dimensions (about 0.1 to 1.5 microns) which are too small for convenient use in animal circulatory studies.

Many of the problems associated with the prior art were solved by the development of a tracer particle having an ion exchange resin core with a controlled thickness polymer coating as described in U.S. Pat. No. 4,107,283. These tracer particles were found to be non-agglomerating in an injectable suspension, and when used in vivo or when stored in dry form. Although the controlled thickness polymer coating provides substantial non-leaching characteristics to the tracer particles described in U.S. Pat. No. 4,107,283, there still remains undesirable leaching of some radionuclides from the ion exchange resin core, particularly under certain conditions such as storage in solution at room temperature or in vivo use at body temperatures. Thus, these particles when labelled with particular nuclides degrade rapidly in vivo in certain types of animal studies making them unsuitable for use in various experiments.

Thus, there remains a need for improved tracer particles having improved stability against leaching of the radionuclide label during storage and in vivo.

SUMMARY OF THE INVENTION

The present invention provides an improved tracer particle comprising an ion exchange core having a polymer coating thereon, the coated ion exchange core having a reaction site capable of reacting with a compound containing an oxirane group, said coated ion exchange core having been treated with a compound containing an oxirane group to react with said coated ion exchange core causing an increase in mass of the tracer particle. The tracer particles of this invention have improved characteristics including improved stability against leaching and improved handling properties. The tracer particles of this invention are useful in circulatory determinations involving the injection of the particles as a suspension in a physiologically acceptable carrier or medium into the circulatory system of animals.

The animals are normally sacrificed to permit the determination of the distribution of particles throughout the body. The determination of the distribution of particles throughout the body may be made by visual microscopic examination after sacrifice of the animal, by the use of conventional radioactivity counters when radioactive ions are incorporated in the particle or by conventional X-ray fluorescence techniques where the ions are stable nuclides and excited by X-rays to emit characteristic radiation.

Particularly useful tracer particles in accord with the present invention are those labelled with radionuclides such as, for example, Cadmium$^{109}$, Cerium$^{141}$, Chromium$^{51}$, Cobalt$^{57}$, Gadolinium$^{153}$, Indium$^{114m}$, Manganese$^{54}$, Niobium$^{95}$, Ruthenium$^{103}$, Scandium$^{46}$, Strontium$^{85}$, Tin$^{113}$, and the like.

This determination is useful to clinical and medical investigators as a tool for determining blood flow and the affect of drugs, e.g., vasodilators and vasoconstrictors on blood flow. In addition, the tracer particles of this invention may be introduced into process control streams found in the chemical industry to determine the flow of fluid in the stream, e.g. by the making of radioactivity measurements along the length of the stream. The ion exchange cores which can be used in the invention are anionic or cationic organic ion exchange resin cores or inorganic ion exchange cores that have a site for reacting with an oxirane group, either before or after a polymer coating is applied. Cationic organic exchange resin cores are preferred. Many such ion exchange cores are known, and it is well known that they can be obtained in forms which will permit exchange with particular ions, (i.e. labels) or can be placed in such form by treatment with the proper reagent.

DESCRIPTION OF THE INVENTION

The ion exchange cores and polymer coatings useful in the practice of the present invention are those described in U.S. Pat. No. 4,107,283, which is hereby incorporated by reference, and the like, which have reaction sites for an oxirane group, at least when the cores are coated with a polymer such as described in U.S. Pat. No. 4,107,283. Particularly useful ion exchange cores are organic ion exchange resin cores such as the strongly acidic sulfonated polystyrene resins, phenolic resins containing methylene group linked sulfonic groups, polystyrene resins containing phosphonic groups, acrylic resins containing carboxylic groups, and the like. These cores are available in particulate form such as tiny spherules having diameters of the order of 1 to 200 microns and as irregularly shaped particles. Any of such forms can be employed in the process of the invention; and while there are no limitations on the size of particles which can be employed herein, preferably spherical beads or irregular particles of a size of the order of about 10 to 200 microns diameter or maximum dimension are employed. Larger particles can be used for particular, specific purposes; however, as a practical matter the particle size is kept to that which passes through a 50 mesh screen, i.e., about 200 microns. For medical diagnostic or therapeutic purposes, the particles are preferably spherical to prevent unintentional passage of the particles into smaller than intended blood vessels and furthermore, limited to preselected sizes and size distribution.

In animal circulatory studies, the cores preferably have a density between 1 to 1.5 and most preferably about a density of about 1.1 to 1.3 which is close to the density of blood. Broadly speaking, any element radioactive or non-radioactive which is capable of existing as an ion in solution and which can be detected can be employed as a label for the particles of this invention.

Particularly useful radioactive ions are Cadmium[109], Cerium[141], Chromium[51], Cobalt[57], Gadolinium[153], Indium[114m], Manganese[54], Niobium[95], Ruthenium[103], Scandium[46], Strontium[85], and Tin[113] as aforesaid, and others well known in the art. Generally speaking, the ion exchange core in practice would preferably have adsorbed thereon 0.1 to 100 millicuries per gram of core when a radionuclide ion is employed, although other ranges of radioactivity may be used depending upon the application. See Helfferich F., *ION EXCHANGE*, McGraw-Hill Book Company, New York (1962) or other techniques such as shown in U.S. Pat. No. 3,334,050. Non-radioactive nuclides such as strontium, barium, iron, zinc, etc., can also be adsorbed on the cores.

The cores of this invention are preferably labelled with the aforementioned radionuclide ions using conventional batch ion exchange techniques well known in the art. After labelling, the cores are preferably impregnated with polymer by reacting monomer, in situ, within and on the core. The cores are preferably reacted batchwise with monomer to provide the individual or monodispersed coated tracers. As used herein the term monomer is meant to include one or more monomers which react to form a polymer or copolymer. Little, or no, polymerization occurs in the bulk of the monomer solution, even though polymerization is extensive and complete within and on the core. After the coated particles or tracers are separated from the remaining monomer solution, and then rinsed and dried, they are free flowing and monodisperse. The coating can be further cured by heating in an oven at temperatures up to about 110° C. for an appropriate period of time, e.g. 1 to 20 hours.

The monomers which are preferred for use in the practice of this invention are those which are acid catalyzed. The most preferred monomer for this invention is furfuryl alcohol. Other monomers and monomer mixtures useful in this invention include, for example, furfuryl alcohol-formaldehyde, furfural, phenol-formaldehyde, phenol-furfural, phenol-furfuryl alcohol, furfural-acetone, urea-formaldehyde, urea-formaldehyde-furfuryl alcohol, furfural-furfuryl alcohol-phenol, analine-furfural, melamine-formaldehyde, tetrahydrofurfuryl alcohol and melamine-furfural.

Partially polymerized monomer or monomer mixtures can be used in order to achieve extensive and complete polymeric coatings. For example, partially polymerized furfuryl alcohol which can be obtained commercially from Hooker Chemical Company, Durez Division, can also be utilized to apply an effective coating to the particular cores.

Although any coating thickness is useful, it is preferred that the coating thickness should be at least 0.5 microns. In order to achieve this, the ratio of weight of ion exchange core to the weight of monomer is preferably one part ion exchange core to a range of 0.5 to 20 parts by weight of monomer. In practice, the most preferred range for application of furfuryl alcohol as furan polymeric coating is one part by weight ion exchange core to a range of 2 to 10 parts by weight of furfuryl alcohol. These conditions lead to coatings which range from about 0.5 microns to 5 microns in thickness, and preferably range from one to three microns in thickness.

The catalytic ions, e.g. $H^+$, for initiating polymerization of the monomer are normally incorporated in the commercially available ion exchange resins as purchased. Alternatively, the $H^+$ ions can be applied to ion exchange cores by immersing same in HCl, dilute $H_2SO_4$, dilute $HNO_3$ or any other acids conventionally used for this purpose in the art. The ion exchange cores preferably contain, for example, from 1.5 to 5 milliequivalents of $H^+$ per gram of ion exchange cores.

After the polymer coating has been applied, the cores are treated with a compound containing an oxirane group, preferably ethylene oxide. During the treatment the oxirane groups reacts with a reaction site on the coated core causing an increase in mass and volume of the core. The length of time, temperature and concentration of oxirane groups can be varied to obtain the desired degree of treatment. Typically, satisfactory results are obtained by treating the cores in a standard ethylene oxide autoclave at 135°–140° F. for about 5 hours.

The treated cores are typically sterilized by heat autoclave, either dry or in a saline suspension, before use. Satisfactory sterility is typically achieved by autoclaving at 120°–130° C. for about 15 minutes.

Injectable suspensions of the labelled cores are prepared by mixing about 1 mCi (about 100 mg) of the labelled particles in a suitable amount of a physiologically acceptable liquid carrier, e.g. 10% Dextran solution or isotonic saline solution with a trace amount of Tween 80 surfactant to aid dispersion of the particles, so that the concentration in solution is about 0.05 to 0.1 mCi/ml. The resulting suspension is sonicated for about 30 minutes to provide uniform dispersion. A typical injection dose of about 20–25 Ci can be readily obtained by withdrawing a suitable quantity of the suspension which would contain approximately 2.5 mg of particles or about $2 \times 10^5$ particles.

The following examples are provided to further illustrate the invention. Unless otherwise indicated, room temperatures as used in the examples means about 17° to 22° C.

EXAMPLE 1

[85]Strontium Labelled Particles 1.46 grams of cation exchange resin of the sulfonated styrene type in the form of 10–15 micron diameter spherical particles (cores) (Aminex A-5, available from Bio-Rad Laboratories, Richmond, Calif.) was mixed with about 50 ml of solution containing 20 mCi of $^{85}$Sr in 0.01N HCl. After stirring for about 15 minutes, the particles were filtered out of the suspension and dried in an oven at about 110° C. To the dried particles was added 0.688 ml of purified water and the resultant mixture was allowed to equilibrate for at least 6 hours.

To the moisturized particles was added a solution of 25 ml of furfuryl alcohol containing 0.2 g of benzoyl peroxide. An exothermic reaction typically takes place upon mixture. If the room is too cold a heat lamp can be used to start the reaction. The reaction temperature was monitored and after the temperatur peaks, the reaction vessel was placed in a boiling water bath for about 30 minutes. The resulting black particles were then filtered, washed with a hard spray of acetone to break up any clumps of particles, and air dried. The particles were then dried in an oven at 40° C. overnight.

EXAMPLE 2

Other Labels

Particles labelled with $^{57}$Co, $^{114m}$In, and $^{54}$Mn, were made in the same manner as in Example 1 except that 20 mCi of the appropriate label was substituted for $^{85}$Sr.

EXAMPLE 3

Additional Coating of Polymer

In addition to the polymer coating provided by the reaction with furfuryl alcohol as set forth in Example 1, the particles can be provided with an additional coating of polymer (recoated) in the following manner.

To the labelled and coated particles of Example 1 is added 20 ml of 12N H$_2$SO$_4$ and the mixture was stirred for about 1 hour to wet the surface of the particles. The mixture was then sonicated for about 15 minutes after which the particles were filtered out and air dried. The particles were then washed with 5 ml of H$_2$O, twice, and air dried. After drying, the particles were placed in a 100 ml beaker to which 20 ml of furfuryl alcohol was added, and the beaker was placed in a water bath at 80° C. for about 1 hour. The particles are then filtered out, washed with hard sprays of acetone and air dried. Finally, the particles were oven dried at 40° C. overnight.

EXAMPLE 4

Ethylene Oxide Treatment

The labelled particles of Examples 1, 2 or 3 were treated in a standard ethylene oxide autoclave at 57°-60° C. for 5 hours. The ethylene oxide reacts with the particles causing an increase in weight.

EXAMPLE 5

Example 3 were divided into two portions. One portion was treated with ethylene oxide (EO) as described in Example 4 while the second portion was not so treated (NEO). The particles were stored dry for various periods of time, then suspended in saline and treated for leaching of the label into saline and/or into plasma in the following manner:

A. Saline Leach Test

The particles were suspended in 5.0 ml of normal saline containing 0.01% by weight of Tween 80, sonicated for 15 minutes to monodisperse the particles, and autoclaved for 20 minutes at 120°-130° C. to sterilize the suspensions. After cooling the suspensions are assayed. The beginning amounts of particles are calculated to obtain a final amount of about 0.130 mCi of $^{57}$Co and about 0.800 to 0.900 mCi of $^{85}$Sr per 5 ml of suspension.

Samples of the saline are taken at various intervals to determine the amount of radioactivity that has leached out of the particles into the saline.

B. Plasma Leach Test

A sample of the particles (about 100,000 cpm) is withdrawn from the saline solution prepared in 5A above at various times after the saline suspension is prepared. The particles are separated from the saline solution and suspended in 2.0 ml of plasma. After 24 hours in the plasma, 1 ml of plasma is removed and assayed to determine the amount of radioactivity leached out of the particles into the plasma. The 1 ml of plasma is returned. After 48 hours, if desired 1 ml of plasma is again separated from the particles and assayed to determine the amount of radioactivity leached out of the particles into the plasma.

After 5 days in storage samples of particles containing either $^{57}$Co or $^{85}$Sr labels, both treated (EO) and non-treated (NEO), were removed from storage and saline suspensions prepared as described in 5A above. At various times after preparation of the saline suspensions, samples were assayed to determine the percent leach of the label into both saline and plasma. The results are given below in Tables 1 and 2.

TABLE 1

Percent Leach of $^{57}$Co or $^{85}$Sr Into Saline At Various Times (After 5 Days Dry Storage)

| Particle Treatment | Time in Saline (Days) | | | | | | |
|---|---|---|---|---|---|---|---|
| | 0 | 1 | 6 | 13 | 20 | 36 | 50 |
| $^{57}$Co (NEO) | 0.8 | 0.8 | 0.8 | 0.9 | 0.9 | 4.2 | — |
| $^{57}$Co (EO) | 0.3 | 0.3 | 0.3 | 0.3 | 0.3 | 0.5 | 0.7 |
| $^{85}$Sr (NEO) | 0.7 | 0.7 | 0.9 | 0.9 | 0.9 | — | — |
| $^{85}$Sr (EO) | 0.2 | 0.2 | 0.3 | 0.4 | 0.5 | — | — |

TABLE 2

Percent Leach of $^{57}$Co or $^{85}$Sr Into Plasma At Various Times (After 5 Days Dry Storage)

| Particle Treatment | Time In Saline (Days) | | | | | | | | | | | |
|---|---|---|---|---|---|---|---|---|---|---|---|---|
| | 1 | | 7 | | 14 | | 21 | | 36 | | 50 | |
| | 24* | 48* | 24* | 48* | 24* | 48* | 24* | 48* | 24* | 48* | 24* | 48* |
| $^{57}$Co (NEO) | 1.6 | 1.9 | 1.7 | 1.9 | 1.8 | 2.1 | 1.8 | 2.3 | 2.2 | 2.9 | — | — |
| $^{57}$Co (EO) | 0.2 | 0.4 | 0.2 | 0.5 | 0.3 | 0.7 | 0.4 | 0.8 | 0.3 | 0.9 | 0.4 | 0.9 |
| $^{85}$Sr (NEO) | 19.9 | 28.3 | 20.9 | 32.1 | 29.3 | 45.3 | 38.2 | 52.3 | — | — | — | — |
| $^{85}$Sr (EO) | 0.6 | 0.9 | 0.7 | 0.9 | 0.9 | 1.1 | 1.0 | 1.3 | — | — | — | — |

*Time in Plasma (hrs.)

Comparative Stability Tests for $^{57}$Co and $^{85}$Sr Labelled Particles

Particles labelled with $^{57}$Co and with $^{85}$Sr in the manner described in Example 1 and recoated as described in After 12 days in storage samples of particles containing either $^{57}$Co or $^{85}$Sr, both treated and non-treated, were removed from storage and saline suspensions prepared as described in 5A. At various times after preparation of the saline suspensions, samples were assayed to determine the percent leach of the label into both saline and plasma. The results are given below in Tables 3 and 4.

TABLE 3

Percent Leach of $^{57}$Co or $^{85}$Sr Into Saline At Various Times (After 12 Days Dry Storage)

| Particle Treatment | Time In Saline (Days) | | | | | |
|---|---|---|---|---|---|---|
| | 0 | 1 | 8 | 15 | 31 | 45 |
| $^{57}$Co (NEO) | 1.6 | 1.7 | 1.9 | 2.0 | 14.9 | — |
| $^{57}$Co (EO) | 0.5 | 0.5 | 0.7 | 0.8 | 0.9 | 1.4 |
| $^{85}$Sr (NEO) | 2.3 | 2.5 | 2.9 | 3.1 | — | — |
| $^{85}$Sr (EO) | 0.8 | 0.9 | 1.0 | 1.1 | — | — |

TABLE 4

Percent Leach Of $^{57}$Co or $^{85}$Sr Into Plasma At Various Times (After 12 Days Dry Storage)

| Particle Treatment | Time in Saline (Days) | | | | | | | | | |
|---|---|---|---|---|---|---|---|---|---|---|
| | 1 | | 7 | | 14 | | 29 | | 43 | |
| | 24* | 48* | 24* | 48* | 24* | 48* | 24* | 48* | 24* | 48* |
| $^{57}$Co (NEO) | 2.5 | 3.9 | 2.9 | 4.7 | 3.7 | 4.9 | 4.3 | 5.8 | — | — |
| $^{57}$Co (EO) | 0.4 | 0.6 | 0.5 | 0.6 | 0.6 | 0.6 | 0.4 | 0.9 | 0.6 | 1.0 |
| $^{85}$Sr (NEO) | 63.4 | 91.7 | 83.2 | 97.3 | — | — | — | — | — | — |
| $^{85}$Sr (EO) | 10.7 | 26.3 | 17.5 | 35.4 | 24.1 | 51.2 | — | — | — | — |

*Time in Plasma (hrs.)

After 19 days in storage samples of particles containing either $^{57}$Co or $^{85}$Sr, both treated and non-treated, were removed from storage and saline suspensions prepared as described in 5A above. At various times after preparation of the saline suspensions, samples were assayed to determine the percent leach of the label into both saline and plasma. The results are given below in Tables 5 and 6.

TABLE 5

Percent Leach Of $^{57}$Co or $^{85}$Sr Into Saline At Various Times (After 19 Days Dry Storage)

| Particle Treatment | Time In Saline (Days) | | | |
|---|---|---|---|---|
| | 0 | 7 | 24 | 38 |
| $^{57}$Co (NEO) | 2.1 | 2.5 | 29.4 | — |
| $^{57}$Co (EO) | 0.7 | 0.8 | 1.3 | 2.1 |
| $^{85}$Sr (NEO) | 3.9 | 4.3 | — | — |
| $^{85}$Sr (EO) | 1.0 | 1.1 | — | — |

TABLE 6

Percent Leach Of $^{57}$Co or $^{85}$Sr Into Plasma At Various Times (After 19 Days Dry Storage)

| Particle Treatment | Time In Saline (Days) | | | | | | | |
|---|---|---|---|---|---|---|---|---|
| | 1 | | 7 | | 22 | | 36 | |
| | 24* | 48* | 24* | 48* | 24* | 48* | 24* | 48* |
| $^{57}$Co (NEO) | 2.9 | 4.1 | 3.5 | 4.8 | 3.9 | 6.4 | — | — |
| $^{57}$Co (EO) | 0.5 | 0.7 | 0.6 | 0.8 | 0.5 | 1.0 | 0.2 | 1.2 |
| $^{85}$Sr (NEO) | 85.2 | 97.4 | — | — | — | — | — | — |
| $^{85}$Sr (EO) | 20.2 | 45.2 | 32.1 | 53.2 | — | — | — | — |

*Time in plasma (hrs.)

Even after 56 days dry storage prior to suspension in saline, the treated cobalt particles showed only small quantities of leaching: 0.5% leach in saline after one day; 0.1% leach in plasma (24 hours), and 1.1% leach in plasma (72) hours after one day in saline.

EXAMPLE 6

Comparative Stability Tests For $^{114m}$In Labelled Particles

Particles labelled with $^{114m}$In in the manner described in Example 1 and recoated as described in Example 3 were divided into two portions. One portion was treated with ethylene oxide as described in Example 4 (EO) while the second portion was not so treated (NEO). The particles were then stored for various periods of time under various conditions to determine stability by the saline leach test described in 5A above and the plasma leach test described in 5B above.

After one day storage at 0° C., samples of particles were suspended in saline in accord with the procedure described in 5A above. The percent leach in saline was determined at various times and the results are shown in Table 7 below.

TABLE 7

Percent Leach Of $^{114m}$In Into Saline At Various Times (After One Day 0° C., Dry Storage)

| Particle Treatment | Time in Saline (Days) | | |
|---|---|---|---|
| | 1 | 4 | 106 |
| NEO | 0.7 | 0.4 | 4.4 |
| EO | 0.2 | 0.3 | 2.1 |

After four days storage at 0° C., samples of particles were suspended in saline as described above. Saline and plasma leach tests were performed at various times and the results are shown in Tables 8 and 9 below.

TABLE 8

Percent Leach Of $^{114m}$In Into Saline At Various Times (After 4 Days 0° C., Dry Storage)

| Particle Treatment | Time In Saline (Days) | |
|---|---|---|
| | 0 | 106 |
| NEO | 1.1 | 5.2 |
| EO | 0.1 | 2.0 |

TABLE 9

Percent Leach of $^{114m}$In Into Plasma At Various Times (After 4 Days 0° C. Dry Storage)

| Particle Treatment | Time In Plasma (hrs) | |
|---|---|---|
| | 24 | 48 |
| NEO | 0.2 | 0.3 |
| EO | 0.1 | 0.3 |

After 27 days dry storage at 0° C. or at room temperature (RT), samples of particles were suspended in saline and tested for leach into saline and plasma at various times thereafter. The results are shown in Tables 10 and 11 below.

TABLE 10

Percent Leach Of $^{114m}$In Into Saline At Various Times (After 27 Days Dry Storage)

| Particle Treatment | Time In Saline (Days) | | | |
|---|---|---|---|---|
| | 1 | 13 | 20 | 84 |
| 0° (NEO) | 1.0 | 1.3 | 1.4 | 5.1 |
| 0° (EO) | 0.1 | 0.2 | 0.2 | 1.4 |
| RT (NEO) | 1.8 | 2.4 | 2.5 | 9.3 |
| RT (EO) | 0.1 | 0.3 | 0.4 | 2.1 |

TABLE 11

Percent Leach Of $^{114m}$In Into Plasma At Various Times (After 27 Days Dry Storage)

| Particle Treatment | Time In Plasma (hours)* | |
|---|---|---|
| | 24 | 48 |
| 0° (NEO) | 1.3 | 1.5 |
| 0° (EO) | 0.08 | 0.2 |
| RT (NEO) | 2.2 | 3.9 |
| RT (EO) | 0.1 | 0.3 |

*Less than one day in saline prior to test

After 56 days dry storage at 0° C. or room temperature, samples of particles were suspended in saline and tested for leach into saline and plasma at various times thereafter. The results are shown in Tables 12 and 13 below.

TABLE 12

Percent Leach Of $^{114m}$In Into Saline At Various Times (After 56 Days Dry Storage)

| Particle Treatment | Time In Saline (Days) | | |
|---|---|---|---|
| | 1 | 2 | 54 |
| 0° (NEO) | 12.1 | 12.7 | 15.1 |
| 0° (EO) | 0.5 | 0.5 | 1.2 |
| RT (NEO) | 13.1 | 15.3 | 21.4 |
| RT (EO) | 3.0 | 3.8 | 5.2 |

TABLE 13

Percent Leach Of $^{114m}$In Into Plasma At Various Times (After 27 Days Dry Storage)

| Particle Treatment | Time In Plasma (hours)* | |
|---|---|---|
| | 24 | 48 |
| 0° (NEO) | 1.8 | 1.9 |
| 0° (EO) | 0.2 | 0.3 |
| RT (NEO) | 7.4 | 7.1 |
| RT (EO) | 0.4 | 0.5 |

*Less than one day in saline prior to test

After 111 days storage at 0° C. and room temperature, samples of the particles were suspended in saline and tested for leach into saline and plasma. The results are shown below in Tables 14 and 15.

TABLE 14

Percent Leach Of $^{114m}$In Into Saline After First Day In Suspension (After 111 Days Dry Storage)

| Particle Treatment | Time In Saline (Days) |
|---|---|
| | 1 |
| 0° (NEO) | 15.4 |
| 0° (EO) | 1.5 |
| RT (NEO) | 18.4 |
| RT (EO) | 4.1 |

TABLE 15

Percent Leach Of $^{114m}$In Into Plasma After Less Than A Day In Saline (After 111 Days Dry Storage)

| Particle Treatment | Time In Plasma (Hours) | |
|---|---|---|
| | 24 | 48 |
| 0° (NEO) | 0.2 | 0.2 |
| 0° (EO) | 0.02 | 0.03 |
| RT (NEO) | 1.6 | 1.8 |
| RT (EO) | 0.2 | 0.2 |

EXAMPLE 7

Injectable Preparation

An injectable preparation is prepared by suspending 1 mCi (100 mg) of particles prepared as described in Examples 1, 3 and 4 in 20 ml of 10% Dextran solution with a trace amount of Tween 80 surfactant added to insure dispersion of the particles. The resulting suspension was ultrasonicated for approximately 30 minutes to provide uniform dispersion. At this point the suspension was at a concentration of 5 milligrams/milliliter and 0.05 millucuries/milliliter. A typical injection of 20-25 microcuries was obtained by withdrawing approximately 0.5 ml of the suspension, containing approximately 2.5 mg of material or approximately $2 \times 10^5$ particles.

EXAMPLE 8

Injectable Preparation

An injectable preparation was prepared by suspending 1 millicurie (100 mg) of particles prepared as described in Examples 1, 3 and 4 in 10 ml isotonic saline with a trace of Tween 80 surfactant added to insure dispersion of the particles. The resulting suspension was ultrasonicated for 30 minutes to provide uniform dispersion. At this point the suspension was at a concentration of 10 milligrams per milliliter and 0.1 millicuries/milliliter. A typical injection of 20-25 microcuries was obtained by withdrawing approximately 0.25 ml of the suspension containing approximately 2.5 mg of material or approximately $2 \times 10^5$ particles.

EXAMPLE 9

In order to determine blood flow to the oral tissues and brain of a 10.0 kilogram dog, a suspension of approximately six million 15 micron beads (approximately 20 microcuries) prepared as described in Examples 1, 3 and 4 and labelled with $^{57}$Co, consisting of about thirteen milligrams of particles in six ml of 53% solution of sucrose in water is injected by arterial catheterization into the left ventrical of the animal. After about five minutes, the animal is sacrificed and all major organs as well as the brain and oral tissues are excised. Sections of each organ such as kidney, liver and lungs are used as internal controls and are counted with a gamma detector in order to determine flow of each organ. The oral tissues and brain are sectioned and also counted in order to determine the rate of blood flow in milliliters per minute per gram of tissue.

In addition, two arterial blood samples are withdrawn at a known rate from anterior and posterior blood vessels durin injection in order to establish the random nature of the particle distribution in the circulatory system and allow for absolute calculation of blood flow and cardiac output. The bead uptake in brain and oral tissue correlates well with established baseline values for blood flow to these areas of the body. Also, uptake in the other organs is representative of previously established values for flow to these organs.

EXAMPLE 10

In an experiment to determine the cardiac output and blow flow to various organs in rats, a suspension of approximately 50,000 15 micron beads containing about 200,000 dpm of $^{85}$Sr prepared as described in Examples 1, 3 and 4 (approximately 0.1 microcurie) in a volume of 0.25 ml of 63% sucrose is injected into the left ventricle of each of 5 rats. The suspension is prepared by adding 25 ml of 63% sucrose to about 5 million of the beads in the vial, ultrasonicating for 30 minutes, shaking and withdrawing 0.25 ml of the suspension into a syringe.

After a period of approximately 30 seconds, the rats are sacrificed by an intravenous injection of saturated KCl and their hearts are excised, along with other organs, in order to determine the distribution of the microspheres in the animals. This is determined by counting of the organs in a gamma well counter coupled to a single channel analyzer. Results show that the microspheres are situated where expected; i.e., they are located in areas of the rat organs where blood vessel cross sectional diameters were of the order of the mean particle diameters.

In order to determine whether the microspheres remain monodispersed after injection while locating at the various sites, tissue specimens of the heart and other organs are examined with a microscope at 200–400 magnification. The values obtained for total cardiac output and for blood flow to several selected organs (spleen, liver, brain, gut, etc.) are in excellent agreement with values reported previously in the literature obtained with an equivalent product of different manufacture.

The examples above illustrate the substantial improvement in stability of labelled particles which is obtained by treating the particles with a compound containing an oxirane group such as ethylene oxide.

This invention has been described in detail including the preferred embodiments thereof. However, it will be appreciated that those skilled in the art, upon consideraton of this disclosure, may make modifications and improvements within the spirit and scope of this invention.

We claim:

1. An injectable preparation for use in making circulatory measurements, said preparation comprising polymer coated ion exchange cores admixed with a physiologically acceptable liquid carrier, said polymer coated cores having reaction sites for reacting with a compound containing an oxirane group, said polymer cores having bean treated with a compound containing an oxirane group to react with said reaction sites, thereby increasing the mass of said polymer coated cores.

2. The preparation of claim 1 wherein said ion exchange cores are labelled.

3. The preparation of claim 1 wherein said ion exchange cores are labelled with a radioactive nuclide.

4. The preparation of claim 3 wherein said radioactive nuclide is selected from Cadmium$^{109}$, Cerium$^{141}$, Chromium$^{51}$, Cobalt$^{57}$, Gadolinium$^{153}$, Indium$^{114m}$, Manganese$^{54}$, Niobium$^{95}$, Ruthenium$^{103}$, Scandium$^{46}$, Strontium$^{85}$ and Tin$^{113}$.

5. The preparation of claim 3 wherein said ion exchange cores comprise an organic ion exchange resin.

6. The preparation of claim 3 wherein said ion exchange cores comprise a cationic organic ion exchange resin.

7. The preparation of claim 3 wherein said ion exchange cores comprise a sulfonated polystyrene resin.

8. The preparation of claim 3 wherein said oxirane containing compound is ethylene oxide.

9. The preparation of claim 1 in which the cores will pass through a 50 mesh screen.

10. The preparation of claim 9 in which the coating is of a thickness of 0.5 to 5 microns.

11. The preparation of claim 10 in which the coating is of a thickness of 1 to 3 microns.

12. The preparation of claim 1 in which the cores comprise ion exchange resin.

13. The preparation of claim 12 in which the cores are of a diameter of 1 to 200 microns.

14. The preparation of claim 1 wherein said ion exchange cores comprise a cationic organic ion exchange resin.

15. The preparation of claim 1 wherein said ion exchange cores comprise a sulfonated polystyrene resin.

16. The preparation of claim 1 wherein said oxirane containing compound is ethylene oxide.

17. A particle comprising a polymer coated ion exchange core, said polymer coated core having a reaction site for reacting with a compound containing an oxirane group, said polymer coated core having been treated with a compound containing an oxirane group to react with said reaction sites, thereby increasing the mass of said polymer coated core.

18. The particle of claim 17 wherein said ion exchange core is labelled.

19. The preparation of claim 17 wherein said ion exchange cores are labelled with a radioactive nuclide.

20. The preparation of claim 19 wherein said radioactive nuclide is selected from Cadmium$^{109}$, Cerium$^{141}$, Chromium$^{51}$, Cobalt$^{57}$, Gadolinium$^{153}$, Indium$^{114m}$, Manganese$^{54}$, Niobium$^{95}$, Ruthenium$^{103}$, Scandium$^{46}$, Strontium$^{85}$ and Tin$^{113}$.

21. The preparation of claim 19 wherein said ion exchange cores comprise an organic ion exchange resin.

22. The preparation of claim 19 wherein said ion exchange cores comprise a cationic organic ion exchange resin.

23. The preparation of claim 19 wherein said ion exchange cores comprise a sulfonated polystyrene resin.

24. The preparation of claim 19 wherein said oxirane containing compound is ethylene oxide.

25. The preparation of claim 17 in which the cores will pass through a 50 mesh screen.

26. The preparation of claim 25 in which the coating is of a thickness of 0.5 to 5 microns 27. The preparation of claim 26 in which the coating is of a thickness of 1 to 3 microns.

28. The preparation of claim 17 in which the cores comprise ion exchange resin.

29. The particle of claim 28 in which the cores are of a diameter of 1 to 200 microns.

30. The particle of claim 17 wherein said ion exchange cores comprise a cationic organic ion exchange resin.

31. The particle of claim 17 wherein said ion exchange cores comprise a sulfonated polystyrene resin.

32. The particle of claim 17 wherein said oxirane containing compound is ethylene oxide.

33. The particle of claim 17 wherein the polymeric coating comprises a furan polymer.

34. The particle of claim 17 wherein the polymeric coating is the reaction product of an acid catalyzed monomer.

35. A method for making a tracer particle comprising:
contacting an acid catalyzed monomer with an ion exchange core having H+ ions whereby polymerization of said monomer is catalyzed at the surface of said core, thereby forming a coated core; said coated core having a reaction site for reacting with a compound having an oxirane group; and treating said coated core with a compound having an oxirane group to react with said reaction site, thereby increasing the mass of said coated core.

36. The method of claim 35 wherein said core comprises an organic ion exchange resin.

37. The method of claim 36 wherein said resin is a sulfonated polystyrene resin.

38. The method of claim 35 further comprising labelling said ion exchange core prior to said contacting step.

39. The method of claim 38 wherein said labelling step comrpises labelling said core with a radioactive nuclide label.

40. The method of claim 39 wherein said label is selected from Cadmium$^{109}$, Cerium$^{141}$, Chromium$^{51}$, Cobalt$^{57}$, Gadoliniuim$^{153}$, Indium$^{114m}$, Manganese$^{54}$, Niobium$^{95}$, Ruthenium$^{103}$, Scandium$^{46}$, Strontium$^{85}$ and Tin$^{113}$.

41. The method of claim 35 wherein said compound is ethylene oxide.

42. A method for determining the characteristics of a circulatory system, said method comprising introducing into said system particles comprising a radioactive labelled ion exchange core having a polymeric coating to form a coated core; said coated core having been treated with a compound having an oxirane group, thereby increasing the mass of said coated core; and determining the flow of particles in the system at a position removed from the site of introduction of said particles into said system.

43. The method of claim 42 wherein said ion exchange core comprises an organic ion exchange resin.

44. The method of claim 42 wherein said compound containing an oxirane group is ethylene oxide.

45. The method of claim 43 wherein said resin is a sulfonated polystyrene resin.

46. The method of claim 4 wherein said radioactive labelled core comprises a radionuclide selected from Cadmium$^{109}$, Cerium$^{141}$, Chromium$^{51}$, Cobalt$^{57}$, Gadolinium$^{153}$, Indium$^{114m}$, Manganese$^{54}$, Niobium$^{95}$, Ruthenium$^{103}$, Scandium$^{46}$, and Strontium$^{85}$, Tin$^{113}$.

* * * * *